United States Patent [19]

Hagedorn

[11] Patent Number: 4,532,209
[45] Date of Patent: Jul. 30, 1985

[54] PRODUCTION OF PARA-CRESOL
[75] Inventor: Scott Hagedorn, Summit, N.J.
[73] Assignee: Celanese Corporation, New York, N.Y.
[21] Appl. No.: 415,129
[22] Filed: Sep. 7, 1982
[51] Int. Cl.³ .......................... C12P 7/22; C12P 7/42; C12R 1/40
[52] U.S. Cl. .................................. 435/156; 435/146; 435/877
[58] Field of Search .............. 435/146, 155, 156, 877; 568/763, 801; 210/673

[56] References Cited

U.S. PATENT DOCUMENTS 2,727,926 12/1955 Kaeding et al. ..................... 568/801
4,071,398 1/1978 Baierl ............................. 210/673 X

OTHER PUBLICATIONS

Davey, et al., Bacterial Metabolism of para- and meta-Xylene: Oxidation of a Methyl Substituent, Journal of Bacteriology, vol. 19, No. 3, 1974, (pp. 923-929).
Reiner, et al., Metabolism of Benzoic Acid by Bacteria. Accumulation of (-)-3,5-Cyclohexadiene-1,2-diol-1-carboxylic Acid by a Mutant Strain of *Alcaligenes eutrophus*, Biochemistry, vol. 10, No. 13, 1971, (pp. 2530-2536).

*Primary Examiner*—David M. Naff
*Attorney, Agent, or Firm*—Depaoli & O'Brien

[57] ABSTRACT

The present invention provides a process for the production of p-cresol in a quantitative yield, which involves the acidification of an aqueous solution of 4-methylcyclohexa-3,5-diene-1,2-diol-1-carboxylic acid under ambient conditions of temperature and pressure to cause spontaneous decomposition of the starting material to p-cresol. The 4-methylcyclohexa-3,5-diene-1,2-diol-1-carboxylic acid is produced by the conversion of p-xylene with the microorganism, *Pseudomonas putida* Biotype A strain ATCC No. 39119.

5 Claims, No Drawings

PRODUCTION OF PARA-CRESOL

BACKGROUND OF THE INVENTION p-Cresol is a specialty chemical with a market of 77 million pounds per year. It is primarily employed in the synthesis of antioxidants such as butylated hydroxytoluenes, and in the preparation of thermosetting resins such as Resoles and Novolacs. Though cresols can be obtained directly from naphtha fractions of coal and oil it is difficult to separate the meta and para isomers due to their very similar boiling points. To obtain pure p-cresol, toluene is sulfonated with sulfuric acid followed by fusion with sodium hydroxide to yield a slurry that is rich in the para isomer. A final cryogenic crystallization is employed to increase the purity of the p-cresol. Alternatively, toluene can be alkylated to a mixture of cymenes using propylene and a Lewis acid followed by dealkylation to cresol and a final cryogenic separation.

U.S. Pat. No. 2,437,648 describes a process for production of p-cresol which involves oxidation of toluene with hydrogen peroxide in the presence of a catalytically active metal oxide such as osmium tetraoxide.

U.S. Pat. No. 2,727,926 (U.S. Pat. No. Re. 24,848) describes a process which involves converting toluic acid to p-cresol in the presence of a soluble copper catalyst such as copper benzoate.

U.S. Pat. No. 3,046,305 describes a process for converting monoalkylbenzene compounds to p-alkylphenols and p-alkylbenzoic acids which involves reacting a monoalkylbenzene with phosgene to provide p,p'-dialkylbenzophenone, and thereafter reacting the p,p'-dialkylbenzophenone with hydrogen peroxide, acetic anhydride and sulfuric acid to yield p-alkylphenyl ester of p-alkylbenzoic acid, which intermediate is then hydrolyzed to the corresponding p-alkylphenol and p-alkylbenzoic acid products.

Other patents which are of general interest include U.S. Pat. Nos. 2,722,546; 2,903,480; 3,819,725; 3,929,911; 4,061,685; 4,189,602; 4,277,012; and the like; and British Pat. No. 964,980.

There is a continuing research effort to develop new and improved methods for the production of large volume specialty chemicals.

Accordingly, it is an object of this invention to provide a process for the production of p-cresol which is not energy intensive.

It is another object of this invention to provide a microbial metabolic pathway for the conversion of p-xylene to a p-cresol precursor.

Other objects and advantages of the present invention shall become apparent from the accompanying description and Examples.

DESCRIPTION OF THE INVENTION

One or more objects of the present invention are accomplished by the provision of a process for the production of p-cresol which comprises providing a reaction medium comprising an aqueous solution of 4-methylcyclohexa-3,5-diene-1,2-diol-1-carboxylic acid, and increasing the acidity of the aqueous solution to a pH level sufficient to convert the said carboxylic acid compound to p-cresol.

The conversion of 4-methylcyclohexa-3,5-diene-1,2-diol-1-carboxylic acid to p-cresol is illustrated by the following reaction scheme:

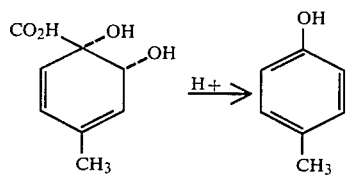

The aqueous medium optionally can contain a water-miscible organic solvent such as ethanol, tetrahydrofuran, acetone, or the like.

The acidic pH of the reaction medium preferably is less than about 6.5, and most preferably is less than about 3. The reaction temperature will be in the range between about 0°–100° C., and normally the reaction proceeds readily at ambient temperatures.

The 4-methylcyclohexa-3,5-diene-1,2-diol-1-carboxylic acid in the aqueous reaction medium converts rapidly and essentially quantitatively at room temperature when the acidity of the aqueous reaction medium is adjusted to less than about 3. A mineral acid such as hydrochloric acid is a convenient reagent for acidification of the aqueous reaction medium.

As demonstrated in Example II, at a neutral pH of about 7 the 4-methylcyclohexa-3,5-diene-1,2-diol-1-carboxylic acid compound is stable and does not spontaneously convert into p-cresol. If the same aqueous medium is heated to a temperature above about 60° C., then the decomposition of carboxylic acid compound to p-cresol occurs.

The recovery of p-cresol from the aqueous medium can be accomplished by conventional means, e.g., by extraction with a water-immiscible solvent such as benzene or ethyl acetate.

An alternative method of recovering p-cresol when present in a low concentration is by contacting the aqueous medium with an adsorbent such as activated charcoal. Subsequently the adsorbed p-cresol can be stripped from the adsorbent substrate by washing with a desorbing agent such as an alkanol (e.g., methanol) or an alkaline solution, or the like. The product adsorption and adsorbent regeneration procedures described in U.S. Pat. No. 4,071,398 are applicable for p-cresol recovery in accordance with the present invention process embodiments.

The 4-methylcyclohexa-3,5-diene-1,2-diol-1-carboxylic acid starting material described herein is related in chemical structure to a novel type of compounds which have been proposed in the literature as microbial cell culture metabolic intermediates having spectral characteristics consistent with a dihydrodiol configuration.

A dihydrodiol of an aromatic carboxylic acid was first reported in Biochemistry, 10, (13), 2530 (1971). A mutant strain of *Alcaligenes eutrophus* blocked in benzoic acid catabolism converted benzoic acid into a compound which has been assigned the structure 3,5-cyclohexadiene-1,2-diol-1-carboxylic acid:

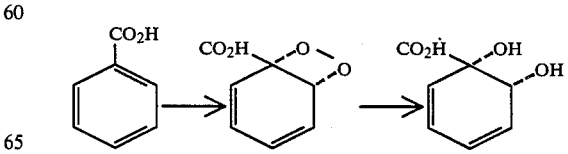

The same publication reports further that the proposed dihydrodiol compound illustrated above decomposed when an acidic aqueous solution of the compound was warmed to 45° C.:

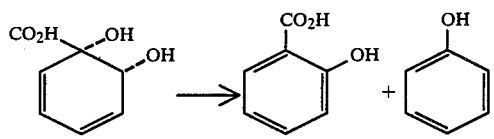

Further, a mutant strain of *Alcaligenes eutrophus*, when induced with benzoic acid, oxidized m-toluic acid to a product which exhibited spectra consistent with the structure 3-methylcyclohexa-3,5-diene-1,2-diol-1-carboxylic acid. In addition, an enzyme prepared from the wild-type organism catalyzed the conversion of the proposed 3-methylcyclohexa-3,5-diene-1,2-diol-1-carboxylic acid to 3-methylcatechol.

A study of a bacterial metabolism of p-xylene and m-xylene is reported in Journal of Bacteriology, 119(3), 923 (1974). Pseudomonas Pxy-40, when grown on succinate in the presence of p-xylene, accumulated p-toluic acid in the culture medium. Under the same conditions Pseudomonas Pxy-82 accumulated p-toluic acid and also 4-methylcatechol. By analogy to the Biochemistry, 10(13) 2530 (1971) experimental results previously described hereinabove, a metabolic pathway was proposed for the initial reactions utilized by Pseudomonas Pxy to oxidize p-xylene. The pathway was visualized as proceeding via p-xylene to p-methylbenzyl alcohol to p-tolualdehyde to p-toluic acid to 4-methylcyclohexa-3,5-diene-1,2-diol-1-carboxylic acid to 4-methylcatechol. The latter 4-methylcatechol metabolite was isolated and identified. There was no accumulation or identification of the presumed 4-methylcyclohexa-3,5-diene-1,2-diol-1-carboxylic acid metabolic intermediate.

Thus, with respect to the microbiological literature reviewed above, in the first case a 3,5-cyclohexadiene-1,2-diol-1-carboxylic acid metabolite converted to salicylic acid and phenol. In the second case, the presumed 4-methylcyclohexa-3,5-diene-1,2-diol-1-carboxylic acid compound was a transitory metabolite intermediate which converted in vivo to 4-methylcatechol. It was unexpected that in accordance with the present invention process 4-methylcyclohexa-3,5-diene-1,2-diol-1-carboxylic acid could be converted rapidly and quantitatively to p-cresol.

As described more fully in Example I of the present specification, a microorganism was employed to convert p-xylene to a metabolic intermediate, i.e., 4-methylcyclohexa-3,5-diene-1,2-diol-1-carboxylic acid, which accumulated in the culture medium.

The microorganism employed was a strain isolated from soil for its ability to grow on toluene. This strain also grows on p-xylene via p-toluate and 4-methylcatechol as metabolic intermediates. Species of Pseudomonas isolated from soil are frequently found to possess plasmids carrying the genes coding for the oxidation of toluene to central metabolites. Plasmids are separate pieces of circular DNA which are smaller than the chromosomal DNA. The particular plasmid of interest has been termed the TOL plasmid, and it codes for the degradation of toluene, p-xylene, m-xylene, benzoate, p-toluate and m-toluate.

The basal medium employed for purposes of the present invention to accumulate and provide the desired 4-methylcyclohexa-3,5-diene-1,2-diol-1-carboxylic acid starting material generally corresponded to that described in Biochem. Biophys. Res. Comm., 36, 179 (1969). p-Xylene was introduced into the culture medium employing sterilized propylene vials.

As a general procedure, strains demonstrating mutant characteristics as determined by the inability to grow on p-xylene were grown on succinate, and then were given p-xylene. The strains of interest were those that appeared to accumulate the greatest amount of 4-methylcyclohexa-3,5-diene-1,2-diol-1-carboxylic acid without the accumulation of 4-methylcatechol.

By means of a chemostat, a strain of p-xylene oxidizing Pseudomonas was isolated which exhibited an increased growth rate. The upgraded strain grew with a doubling time which was seven times shorter than that of the parent strain.

The following Examples are further illustrative of the present invention. The reactants and other specific ingredients and conditions are presented as being typical, and various modifications can be devised in view of the foregoing disclosure within the scope of the invention.

EXAMPLE I

This Example illustrates the microbial culture accumulation of 4-methylcyclohexa-3,5-diene-1,2-diol-1-carboxylic acid from para-xylene metabolism.

The microorganism is *Pseudomonas putida* Biotype A which is isolated from soil by enrichment for growth on toluene. The same microorganism also has the ability to grow on p-xylene, m-xylene, p-toluate and benzoate (ATCC No. 39,119).

A neutral pH culture medium is provided which has the following composition:

| | |
|---|---|
| 50 mM | Na—K Phosphate Buffer |
| 2.0 g/liter | NH$_4$Cl |
| 0.200 | MgSO$_4$.7H$_2$O |
| 0.001 | FeSO$_4$.7H$_2$O |
| 0.003 | MnSO$_4$.H$_2$O |
| 0.003 | ZnSO$_4$.7H$_2$O |
| 0.001 | CoSO$_4$.7H$_2$O |
| 0.010 | EDTA |

A 250 ml Erlenmeyer flask containing 50 ml of the above minimal salts phosphate buffered pH 7.0 sterile liquid culture medium is inoculated with the above described organism from a nutrient agar culture. P-xylene is added to a sterilized polypropylene liquid nitrogen storage vial which is then placed in the inoculated flask. When growth is observed as evidenced by an increase in cell turbidity, a sample is withdrawn from the growing liquid culture, centrifuged and the supernatant is analyzed for metabolic products.

The metabolic product 4-methylcyclohexa-3,5-diene-1,2-diol-1-carboxylic acid is characterized by the following properties:

UV spectrum: $\lambda$max=265 nm; $\epsilon$=3,000 cm$^{-1}$M$^{-1}$.

High Performance Liquid Chromatography (HPLC) Retention Time=5.00–5.15 minutes

Conditions of HPLC:
  Column: C18 Radial Compression HPLC Column (Waters Associates)
  Solvent: 5% Isopropanol and 10 mM Phosphoric Acid
  Flow Rate: 3 ml/min.

The assignment of a vicinal-dihydrodiol configuration to the identified metabolite product is consistent with the pertinent literature. Bacterial catabolism initiated by double hydroxylation yielding cis-configurated dihydrodiols is described in Crit. Rev. Microbiol., 1, 199 (1971) and Tetrahedron, 34, 1707 (1978).

EXAMPLE II

This Example illustrates the invention process for conversion of 4-methylcyclohexa-3,5-diene-1,2-diol-1-carboxylic acid to p-cresol, and effect of pH and temperature on the decomposition reaction.

An aqueous solution of 4-methylcyclohexa-3,5-diene-1,2-diol-1-carboxylic acid is divided into sample portions. The acidification of selected samples is accomplished with phosphoric acid. The heating of selected samples is at a temperature of about 80° C. for 5 minutes. In the following tabulation, the minus sign represents absence of the compound in the final product medium, and the plus sign represents the presence of the compound in the final product medium.

|  | Dihydrodiol* | p-Cresol |
| --- | --- | --- |
| pH 2.0 | − | + |
| pH 7.0 | + | − |
| pH 10.0 | + | − |
| pH 7.0 + heat | − | + |
| pH 10.0 + heat | + | − |
| pH 10 + heat + readjustment to pH 2.0 | − | + |

*Dihydrodiol is determined by HPLC using a C18 column and 5% isopropanol + 10 Mm phosphoric acid as a solvent (retention time, 5.00–5.15 minutes at a flow rate of 3 ml/min).

Activated charcoal is found to adsorb greater than 99 percent of the p-cresol in a 10 Mm aqueous solution. About 35–40 percent of the adsorbed p-cresol is desorbed and recovered by contacting the charcoal with methanol.

What is claimed is:

1. A process for the production of p-cresol which comprises providing a reaction medium comprising an aqueous solution of 4-methylcyclohexa-3,5-diene-1,2-diol-1-carboxylic acid by conversion of P-xylene with the microorganism, *Psudomonas putida* Biotype A strain ATCC No. 39119 and increasing the acidity of the aqueous solution to a pH level of less than about 3 sufficient to convert said 4-methylcyclohexa-3,5-diene-1,2-diol-1-carboxylic acid to p-cresol at a temperature between about 0°–100° C.

2. A process in accordance with claim 1 wherein the conversion of 4-methylcyclohexa-3,5-diene-1,2-diol-1-carboxylic acid to p-cresol is essentially quantitative.

3. A process in accordance with claim 1 wherein the p-cresol product is removed from the aqueous medium by contact of the aqueous medium with a solid adsorbent.

4. A process in accordance with claim 3 wherein the solid adsorbent is charcoal.

5. A process in accordance with claim 3 wherein the p-cresol is subsequently desorbed from the solid adsorbent with alkanol.

* * * * *